United States Patent [19]
Sigoloff

[11] Patent Number: 6,149,685
[45] Date of Patent: Nov. 21, 2000

[54] HUMAN EYE PROSTHESIS

[76] Inventor: Bruce Sigoloff, P.O. Box 17944, San Antonio, Tex. 78217

[21] Appl. No.: 09/346,422

[22] Filed: Jul. 1, 1999

[51] Int. Cl.$^7$ ...................................................... G02C 7/04
[52] U.S. Cl. ............................................. 623/4.1; 351/162
[58] Field of Search ................................ 623/4.1; 351/162

[56] References Cited

U.S. PATENT DOCUMENTS

| | | | |
|---|---|---|---|
| 4,576,453 | 3/1986 | Borowsky | 351/162 |
| 4,652,099 | 3/1987 | Lichtman | 351/162 |

*Primary Examiner*—David H. Willse
*Assistant Examiner*—Suzette J. Jackson
*Attorney, Agent, or Firm*—Jackson Walker L.L.P.

[57] ABSTRACT

A prosthesis for an eye of a wearer formed from a thin film sheet sufficient to cover a portion of the sclera of the eye. The sheet has a number of sections which create the impression that the eye is generally centered within the eye socket. Various embodiments include a section for permanent affixation to the exterior of the eye, a lens section to enhance vision, protection from ultra violet exposure, and a simple masking embodiment which allows the wearer to see through the film with the outer surface of the film having indicia of sclera, iris, and pupil all properly centered.

10 Claims, 2 Drawing Sheets

HUMAN EYE PROSTHESIS

BACKGROUND OF THE INVENTION

This invention relates to a prosthesis for misalignment of the human eye. This present invention provides a cosmetic device or prosthesis which is not intended to correct eye misalignment, but to cover the eye and create an appearance of eye alignment. More particularly, the present invention is a cosmetic device to partially cover the user's iris and sclera to create the impression that the eye is centered in situations where the user suffers from strabismus, the misalignment of the eye; i.e., esotropia (eye turns inward), extropia (eye turns outward), hypertropia (eye turns upward), hypotropia (eye turns downward), and all other conditions which cause cosmetic abnormality with eye misalignment, ocular and neurological.

The user changeable, (disposable) or permanent prosthesis may be placed on top of the eye (disposable) or implanted on the exterior surface of the eye (permanent), and appear as a pupil/iris centered on the sclera (white area of the eye). The device partially covers the user's iris and sclera, but not to affect vision, giving the illusion of the pupil/iris being aligned and centered in the sclera. The device may be provided in a multitude of shapes, sizes and color shades to match the user's pupil-iris-sclera natural appearance. A prescription to correct vision can also be incorporated into the prosthesis to combine the user's prescribed, corrected vision in conjunction with this cosmetic alignment. The device would be available as non-vision correcting or as vision correcting, non-UV blocking or UV blocking.

Strabismus is a common condition among children, with 4% of all children in the United States having some form of strabismus. The condition may also arise later in life. It occurs equally in females and males.

Treatment of strabismus is intended to preserve vision, straighten the eyes, and restore binocular vision (two-eyed) vision. An ophthalmologist may recommend eyeglasses, surgery to correct the unbalanced eye muscles, or cover or patch the strong eye to improve amblyopia (reduced vision in the weaker eye). A new drug, approved by the U.S. Food and Drug Administration for limited use, is an alternative to eye muscle surgery for some individuals. An injection of this drug into an eye muscle temporarily relaxes the muscle, allowing the opposite muscle to tighten and straighten the eye. Normally, the effects of the drug wear off after several weeks. Current treatments often require considerable time to correct the malady, and may be unsuccessful. Thus, the individual treated for strabismus may continue to have eye-misalignment.

It is well known that poor eye alignment is socially noticeable and may lead to psychological problems in both children and adults. Studies indicate that successful surgery for socially noticeable strabismus appears to achieve major improvements in the quality of psychosocial functioning for the majority of adults undergoing such surgical procedures. Again, however, such surgical procedures may not correct the problem. Thus, those suffering from strabismus are provided, through this invention, with a means for reducing the socially noticeable defect.

SUMMARY OF THE INVENTION

The present invention provides a prosthesis for an eye of a wearer formed from a thin film sheet sufficient to cover a portion of the sclera of the eye. The sheet film is thin enough to allow sufficient oxygen transmission therethrough to provide satisfactory morphology of the eye. The sheet has a number of sections which create the impression that the eye is generally centered within the socket. A first outer section of the prosthesis has a first color shade generally corresponding to the color shade of the sclera of the eye of the wearer. The second inner section has a second color shade generally corresponding to the color shade of the iris of the eye of the wearer. A third innermost section is alignable to overlay the pupil of the eye. The various sections overlay the corresponding structures, (sclera, iris, pupil), of the eye, thereby creating an appearance of eye alignment. This present invention provides a cosmetic device or prosthesis which is not intended to correct eye misalignment, but to cover the eye and create an appearance of eye alignment.

DETAILED DESCRIPTION OF THE PREFERRED EMBODIMENT

Figure 1:
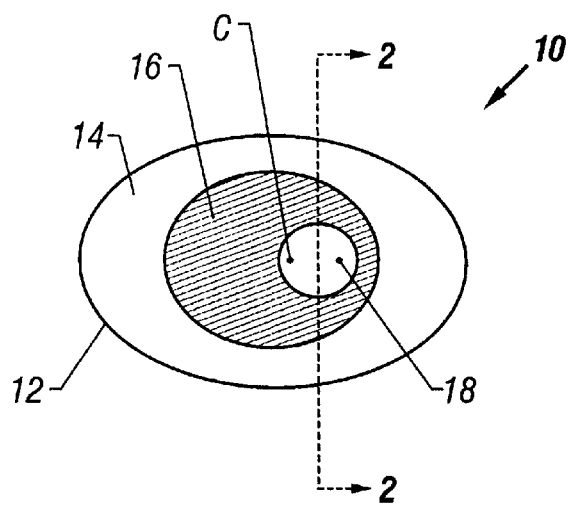
FIG. 1 illustrates a top view of the prosthesis of the present invention.

The present invention 10 is shown in FIG. 1 as a sheet of film 12 having a generally oval shape which would conform to the noticeable portion of the sclera of the human eye. The composition for sheet 12 should be compatible with the eye membranes and not abrasive to the cornea. Such compositions are well known in the art. It will be understood that any number of outer shapes may be employed so long as the sheet fits comfortably in the eye socket against the eye membranes. An outer section 14 of the sheet 12 has a color shade corresponding to that of the sclera of the wearer. Thus, a number of shades may be provided, just as is known in shade matching with any cosmetic material. In one embodiment of the present invention (FIG. 5) the cosmetic prosthesis of the present invention may be permanently affixed to the exterior surface of the eye.

An inner section 16 of the sheet 12 has a color shade corresponding to that of the iris of the wearer. Again, a number of shades may be provided. The inner section 10 is configured to generally align with the iris of the eye and overlay a portion of the iris.

The shape of the human iris is generally circular, but in the present invention the shape of the second inner section 16 may be varied to oblong or elliptical or any shape necessary to create the impression that the wearer's eyes are centered. It will be understood that the actual eye alignment laying beneath the prosthesis of the present invention cannot be moved without other significant treatment of the eye; therefore, it is an object of the present invention to create the cosmetic impression of centering.

A third innermost section 18 is alignable to overlay the entire pupil of the eye. This third section 18 is generally offset from the center C of the second section 16. The third section 18 may be an open orifice through which the natural pupil may accept light in an unhindered manner and through which the natural shade of a portion of the actual iris may be exposed. Further, the third section may be provided with a lens body 18A (FIG. 2) having an optical topography, density, thickness, color, polarization or the like to provide visual enhancement of the eye.

Figure 2:
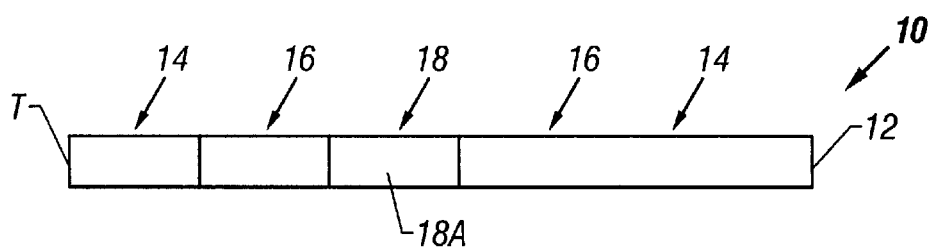
FIG. 2 is a cross-sectional view of the prosthesis of the present invention taken along line 2—2 of FIG. 1.

FIG. 2 illustrates a cross-sectional view of the invention 10 showing the thickness T of the film sheet 12. The film must be thin enough to allow sufficient oxygen transmission through it to ensure that satisfactory morphology of eye is maintained.

Figure 3:
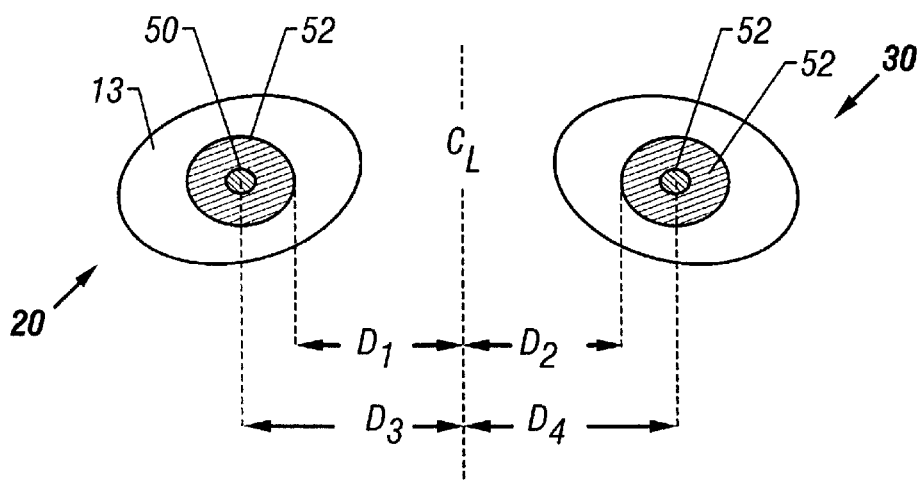
FIG. 3 is a front elevation view of a set of eyes showing misalignment.

FIG. 3 shows the arrangement of human eyes 20 and 30 in a person with strabismus. In FIG. 3 the right eye is turned inwardly slightly (esotropia) to the centerline CL of the eye sockets. The natural pupil 50 and iris 52 are shown. The distance from the centerline CL to the center of the right eye pupil is $D_3$. The distance from the centerline CL to the center of the left eye pupil is $D_4$. The distance from the inner edge of the right eye iris to the centerline CL is $D_1$ while the distance from the inner edge of the left eye iris to the centerline CL is $D_2$.

Figure 4:
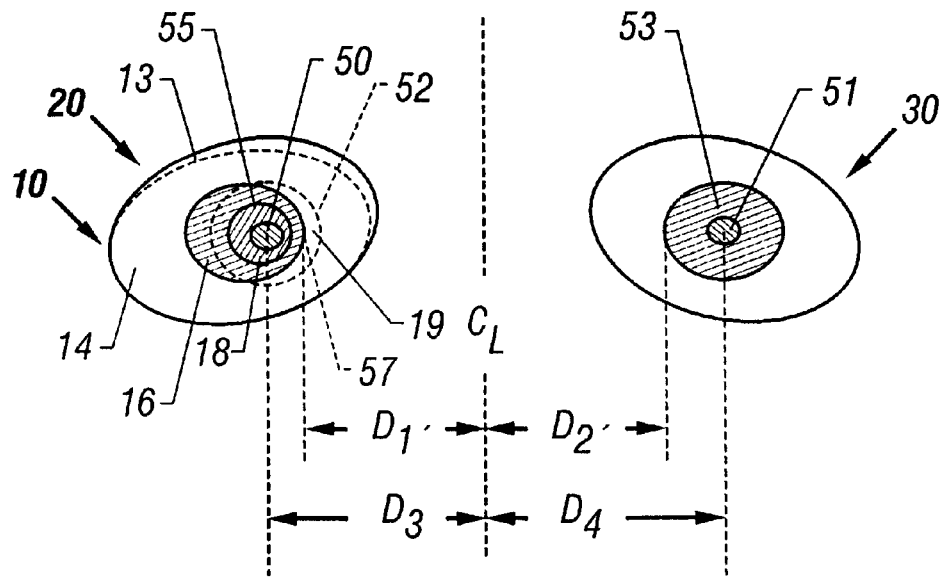
FIG. 4 shows the placement of the present invention over the right eye of FIG. 3 thereby illustrating the impression of centering.

FIG. 4 shows the placement of the prosthesis 10 of the present invention on the right eye 20. The second inner section 16 of the prosthesis 10 is now arranged so that the impression of the misalignment is significantly reduced. Although the pupil 50 of the eye has not been centered, the alignment of the outer section 14 and the second section 16 overlaying a portion of the iris 52 gives the impression of centering. The natural shade of the iris is exposed through a portion 55 of the third section 18 of the cosmetic prosthesis 10 and a portion 57 of the natural iris 52 is covered by a portion 19 of the outer section (sclera) of the prosthesis 10. While $D_3$ and $D_4$ remain the same, it may be seen that $D_1^1$ is greater than $D_2^1$ and that $D_1^1$ and $D_2^1$ are substantially equal.

Figure 5:
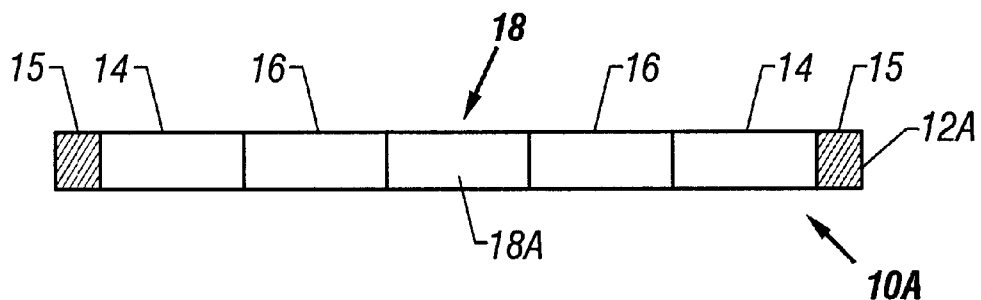
FIG. 5 illustrates a side elevation view of an alternative embodiment of the present invention.

FIG. 5 illustrates that the film sheet 12A of prosthesis 10A (an alternative embodiment) is provided with an outer edge 15 which easily accepts sutures and is of a composition compatible for grafting the eye membranes. The embodiment of 10A is intended to be permanently affixed to the exterior of the eye.

Figure 6:
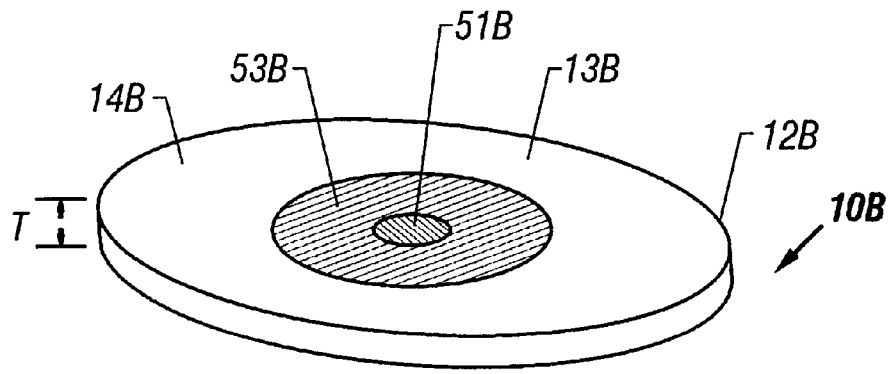
FIG. 6 illustrates a top perspective view of another embodiment of the present invention which allows the wearer to see through the prosthesis.

FIG. 6 illustrates an embodiment of 10B of the present invention wherein the film sheet 12B is constructed from a composition which allows the wearer to see through the film, while the top surface 13B appears opaque. The film 12B partially or entirely covers the sclera, iris and pupil. The surface 13B has the indicia of a properly centered iris 53B and properly centered pupil 51B with the remainder of the film surface 13B appearing as sclera 14B. This embodiment 10B allows the wearer to completely center the pupil 51B in the socket, regardless of the location of the wearer's actual pupil. Embodiment 10B eliminates the need for precise alignment of the film 12B within the eye socket.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

What is claimed is:

1. A cosmetic prosthesis for an eye socket of an eye of a wearer comprising:

a thin film sheet sufficient to cover a portion of the sclera of said eye, said sheet further comprising:
  a first outer section having a first color shade;
  a second inner section having a second color shade, said second inner section alignable to overlay a portion of the iris of said eye; and
  a third innermost section alignable to overlay the pupil of said eye,
said film being thin enough to allow sufficient oxygen transmission therethrough to provide satisfactory morphology of the eye of said wearer.

2. The prosthesis of claim 1 wherein said third innermost section has a diameter generally larger than the diameter of said pupil of said eye and a center of said third section is offset from a center of said second section.

3. The prosthesis of claim 1 wherein said first color shade is generally the same as the color shade of said sclera of said eye, and said second color shade is generally the same as the color shade of said iris of said eye.

4. The prosthesis of claim 1 wherein said sheet is releaseably secured to said eye.

5. The prosthesis of claim 1 wherein said film has a means for surgical affixment to said eye.

6. The prosthesis of claim 1 wherein said third innermost section further comprises a lens body having an optical topography on at least one surface of said lens body to provide visual enhancement to said eye.

7. The prosthesis of claim 1 wherein said third innermost section further comprises an ultraviolet blocker.

8. The prosthesis of claim 1 wherein the second inner section is shaped to create an impression that said second inner section is centered within said socket of said eye.

9. The prosthesis of claim 1 wherein said film sheet is sufficiently transparent to enable said wearer to see through said film sheet.

10. The prosthesis of claim 1 wherein said third innermost section is alignable to overlay said pupil entirely.

* * * * *